(12) United States Patent
Charm et al.

(10) Patent No.: US 6,475,805 B1
(45) Date of Patent: Nov. 5, 2002

(54) METHOD FOR DETECTION OF AN ANALYTE

(75) Inventors: Stanley E. Charm, Boston, MA (US); Richard Skiffington, North Reading, MA (US); Robert J. Markovsky, Kingston, NH (US); Eliezer Zomer, Newton, MA (US); Steven J. Saul, Arlington, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 09/542,203

(22) Filed: Apr. 4, 2000

Related U.S. Application Data

(60) Continuation of application No. 09/389,572, filed on Sep. 3, 1999, now abandoned, which is a division of application No. 09/001,775, filed on Dec. 31, 1997, now Pat. No. 5,985,675.

(51) Int. Cl.$^7$ ............................................. G01N 33/543
(52) U.S. Cl. .......................... 436/514; 422/56; 422/58; 422/187; 422/188; 422/104; 422/110; 422/287; 435/7.1; 435/7.2; 435/7.8; 435/7.92; 435/7.94; 435/7.95; 435/174; 435/287; 435/970; 435/971; 435/7.93; 436/518; 436/524; 436/538; 436/535; 436/810; 436/807
(58) Field of Search ............................ 422/56, 58, 187, 422/188, 104, 110; 435/7.1, 7.2, 7.8, 7.92, 7.94, 7.95, 174, 287, 970, 971, 7.93; 436/518, 524, 538, 530, 535, 533, 810, 807

(56) References Cited

U.S. PATENT DOCUMENTS

| | | |
|---|---|---|
| 4,700,714 A | 10/1987 | Fuisz .......................... 128/767 |
| 4,703,017 A | 10/1987 | Campbell et al. ........... 436/501 |
| 4,743,560 A | 5/1988 | Campbell et al. ........... 436/501 |
| 4,826,759 A * | 5/1989 | Guire et al. |
| 4,999,285 A | 3/1991 | Stiso .......................... 435/7.9 |

(List continued on next page.)

FOREIGN PATENT DOCUMENTS

| | | |
|---|---|---|
| EP | 0 279 574 A1 | 8/1988 |
| EP | 0 291 176 B1 | 11/1988 |
| EP | 0 291 194 B1 | 11/1988 |
| EP | 0 299 428 A2 | 1/1989 |
| EP | 0 306 336 A2 | 3/1989 |
| EP | 3 321 145 A2 | 6/1989 |
| EP | 0 378 391 | 7/1990 |
| EP | 0 582 231 A1 | 2/1994 |
| EP | 0 593 112 B1 | 4/1994 |
| EP | 0 284 232 B1 | 6/1995 |
| WO | WO 90/15327 | 12/1990 |
| WO | WO 94/02850 | 2/1994 |
| WO | WO 96/38720 | 12/1996 |
| WO | WO 97/03209 | 1/1997 |
| WO | WO 97/05287 | 2/1997 |

OTHER PUBLICATIONS

Brady et al., Journal of Food Protection, 56(3):229–233, Mar. 1993.
Charm et al., Journal of the Association of Food and Drug Officials, 58(1), 17–29, Jan. 1994.

(List continued on next page.)

*Primary Examiner*—Bao-Thuy L. Nguyen
(74) *Attorney, Agent, or Firm*—Leslie Meyer-Leon, Esq.; IP Legal Strategies Group P.C.

(57) ABSTRACT

A test device, system and method, the device composed of an elongated, toothbrush-shaped, transparent, plastic housing and a lateral-flow test strip for the detection of an analyte, such as a beta-lactam in milk, in the housing, the housing having an expansion cavity to receive expanded, liquid-contacted, absorbing material in the test strip, and to control lateral flow rate and times in the test strip.

28 Claims, 7 Drawing Sheets

U.S. PATENT DOCUMENTS

| | | | |
|---|---|---|---|
| 5,238,652 A | 8/1993 | Sun et al. ..................... 422/61 |
| 5,260,222 A | * 11/1993 | Patel et al. |
| 5,266,497 A | 11/1993 | Imai et al. .................. 436/514 |
| 5,434,053 A | 7/1995 | Piasio ......................... 435/79 |
| 5,451,504 A | 9/1995 | Fitzpatrick et al. .......... 435/7.2 |
| 5,521,102 A | 5/1996 | Boehringer et al. ........ 436/523 |
| 5,591,645 A | 1/1997 | Rosenstein ................. 436/514 |
| 5,602,040 A | 2/1997 | May et al. .................. 436/514 |
| 5,622,871 A | 4/1997 | May et al. .................. 436/514 |
| 5,656,448 A | 8/1997 | Kang et al. ................ 435/7.94 |
| 5,656,502 A | * 8/1997 | MacKay et al. |
| 5,714,389 A | 2/1998 | Charlton et al. ............ 436/514 |
| 5,726,010 A | 3/1998 | Clark ............................ 435/5 |
| 5,726,013 A | 3/1998 | Clark ............................ 435/5 |
| 5,739,041 A | 4/1998 | Nazareth et al. ............ 436/514 |
| 5,753,517 A | 5/1998 | Brooks et al. .............. 436/514 |
| 5,985,675 A | * 11/1999 | Charm et al. |
| 6,001,658 A | 12/1999 | Frederickson ............... 436/514 |
| D419,439 S | 1/2000 | Markovsky et al. ......... D9/415 |
| 6,177,281 B1 | 1/2001 | Manita ....................... 436/518 |

OTHER PUBLICATIONS

Charm et al., J. Assoc. Off. Anal. Chem., 71(2), 1988.

Hassnoot et al., "Evaluation of a Sol Particle Immunoassay (SPIA) Based Single–Step Strip Test for the Detection of Sulfadimidine Residue," Euro Residue III (1996) 461–465.

"A Short Guide—Developing Immunochromatographic Test Strips," 1996, Lit. No. TB500, Millipore Corporation, Bedford, MA, USA.

Verheijen et al., "Single–Step Strip Tests for Residue Analyses," DLO–State Institute for Quality Control of Agricultural Products (RIKILT–DLO) (Jun. 3, 1998).

* cited by examiner

METHOD FOR DETECTION OF AN ANALYTE

REFERENCE TO PRIOR APPLICATIONS

This application is a continuation of U.S. patent application Ser. No. 09/389,572, filed on Sep. 3, 1999 abandoned, which is a divisional application of U.S. patent application Ser. No. 09/001,775, filed Dec. 31, 1997, now U.S. Pat. No. 5,985,675, issued Nov. 16, 1999.

BACKGROUND OF THE INVENTION

There are numerous patents and publications which describe various lateral-flow or immunochromatographic test kits and methods for the detection of the presence or concentration of chemical residues or analytes or classes thereof from liquid samples. One publication includes "A SHORT GUIDE—developing Immunochromatographic Test Strips" by Millipore Corporation, Bedford, Mass., while U.S. patents would include U.S. Pat. No. 4,703,017, issued Oct. 27, 1987; U.S. Pat. No. 5,591,645, issued Jan. 7, 1997; U.S. Pat. No. 5,266,497, issued Nov. 30, 1993; U.S. Pat. No 4,999,285, issued Mar. 12, 1991; U.S. Pat. No. 5,238,652 issued Aug. 24, 1993; and U.S. Pat. No. 5,622,871, issued Aug. 22, 1997 (all hereby incorporated by reference).

U.S. Pat. No. 5,622,871 describes analytical test devices for biological fluids which include elongated, rectangular, hollow casings to contain a test strip, and which casings have an aperture to permit visual observation of the test results on the test strip. The casings include a protective, removable cap to protect and enclose the application end of the casing. The internal constructional details of the housing are not a significant feature of the invention, but are employed to provide a housing for the particular test strip (column 12, lines 20–26).

It is desired to provide a new and improved analyte test device and method based on test strips in which the housing of the test strip is designed to promote the absorption, flow and efficiency of the test device and the tests carried out.

SUMMARY OF THE INVENTION

The invention relates to an analyte or chemical residue test device and method employing a lateral-flow test strip for the detection of the analyte or residue within a housing and a method therefor.

The invention comprises an analyte test device for detecting, in the general horizontal position, an analyte in a liquid sample by capillary lateral flow in an inmunochromatographic test strip, which device comprises an elongated housing defining an elongated strip cavity having a one open application aperture at one end and having another end, the cavity adapted to receive and hold a test strip therein, and having a transparent top cover section, to permit the observation of test results on the test strip, the housing characterized by an enlarged application cavity extending outwardly from the top cover and having or adapted to have an open end at the application end. The test device includes a test strip positioned in the strip cavity.

The test strip comprises a support strip with a plurality of sequential, contacting, liquid-sample, permeable zones extending from the first to the second ends, which zones permit the lateral capillary flow of the liquid sample from the first to the second end. The zones include a sample-absorbing and filtering zone composed of an expandable, porous, compressed-material layer which moves, on contact with the liquid sample, between a nonexpanded state and an expanded state on absorption of a preselected amount of the liquid sample, and a releasing zone having a mobile-phase layer thereon with a receptor for the analyte of the liquid sample thereon, typically a visible area, for example, of colored beads. The zones include also a reaction zone having at least one stationary-layer analyte reference or test line, or generally a test and a separate control line thereon for observation, to detect the presence of analytes in the liquid sample, and optionally a disposal zone of a layer of liquid-sample absorbent material for the liquid sample and to induce capillary flow to the second end. The sample-absorbing zone with the compressed material layer is positioned adjacent the application cavity, the compressed-material layer and the application cavity designed to provide the compressed-material layer to absorb a selected amount of liquid sample to be tested and sufficient to carry out the test and to expand from a dry, nonexpanded to a wet, expanded state, and to provide for the said material layer in the wet, expanded state to fill substantially the application cavity and to cause sufficient pressure on the housing walls of the expansion cavity to drive capillary flow of the liquid sample toward the disposal zone in said strip in a selected time period and to restrict flow of the liquid sample in the application cavity to a selected volume, when the open application end of the test device is inserted into a liquid to obtain the liquid sample.

In the invention, one preferred embodiment is the employment of a housing, such as a one-piece, integral, injection-molded, all-transparent, plastic material, with the plastic material selected or designed to be subject to incubator temperatures of 50° C. or more for incubation times; for example, of 2 to 10–15 minutes, depending on the particular test.

The preferred embodiment includes a generally toothbrush-type housing shape, with the enlarged, generally rectangular, toothbrush-type head at the open application end of the housing, with a dry, inert, porous, expandable, liquid-permeable, absorbing material in a generally rectangular layer as an absorbing zone in the test strip; for example, of cellulose or nitrocellulose, positioned beneath the open bottom of the application cavity or chamber. The absorbing layer on contact, such as immersion of the application end of the housing of the test device in a liquid, will absorb a preselected amount of the liquid sample required for the test. The absorbing-layer material will expand; for example, in 1 to 30 seconds, to fill or substantially fill the expansion cavity and contact the surrounding walls of the expansion-cavity housing, to cause sufficient pressure within the expansion cavity and in the expanded state of the material to drive capillary flow laterally in the underlying test strip toward the end of the elongated housing where the test strip is positioned. Thus, proper selection and dimensioning of the expansion cavity and underlying absorbing-layer material which generally mimics two dimensions of the expansion cavity, permits absorbing and filtering of the selected amount of liquid sample for the test strip, and aids in driving the lateral flow of the liquid sample in the test strip in the housing toward the end of the test strip; for example, the disposal zone, to receive the liquid sample where employed. If the absorbing layer does not expand sufficiently to fill or substantially fill the expansion cavity, then lateral or capillary flow rates and times are unsatisfactory; that is, flow rate too slow and time period too long. Where the absorbing layer is used in excess, then excess pressure occurs in the expansion cavity, and the expanded absorbing layer tends to retard the desired lateral flow of the liquid sample.

The housing with the toothbrush-shaped design may comprise a separate, injection-molded housing with an optional end cover, to protect the exposed application end before sampling and after sampling, and in the incubation chamber, to prevent cross-contamination from other sources. The test device with the molded housing enables the user to handle the handle end of the housing and to obtain a liquid sample merely by dipping the open application cavity into a liquid.

The housing also may comprise a toothbrush-shaped design, wherein the expansion cavity is formed in a plastic, usually transparent, blister-type package which is sealed against a flat support, such as a paper strip or another plastic strip, and which encompasses within the blister package the selected test strip. The blister package includes a removable seal strip at the one application end of the enclosed test strip, for peeling or removal prior to use and for the introduction of a selected volume of the liquid to the application-absorbing zone of the test strip while in the blister package. The blister package with the liquid sample and test strip may be incubated in the incubator and the test results observed or read.

In a further embodiment, it has been discovered to be desirable to provide one or more apertures in the housing which defines the expansion cavity, to permit the time-controlled and more rapid absorbing of the liquid sample into the absorbing material for more efficient absorption and to reduce absorption time of the liquid sample. In particular, one or more apertures should be placed on the top cover or surface of the expansion-cavity housing, particularly of the molded housing, rather than on the sides, so that entrapped air, after immersion, will be discharged from the expansion cavity, as the absorbing layer expands into the wet, absorbing, expanded state. While a flat, rectangular strip of absorbing material is shown with a generally rectangular expansion cavity which mimics and provides for the expanded, rectangular strip of the absorbing zone, it is recognized that the size, material, dimensions and shape of the absorbing material and the shape or form of the expansion cavity may vary in the practice of the invention. Typically the open bottom of the expansion cavity is directly above the absorbing layer and usually of about the same width and length dimensions, to permit expansion without restriction of the absorption layer into the expansion cavity.

While a fully transparent top cover is desirable to enclose the test strip and observe or read the test results on the test strip, it is recognized that the top cover may be open or have an aperture to view the test results, or only a section of the top cover be transparent to view the test results, or where applicable, the housing may be modified, so that the test results may be determined by optical or electronic instrument means.

The test device may be packaged for use in a blister-type package or employ a fixed or slidable protective cap at the application end, to protect the test device from contamination prior to use and to protect the test device after contact with the liquid sample and in the incubator (where required in the test), to protect against cross-contamination. The protective cap can be removable and enclose totally the application end of the housing, or merely be slidably extended outwardly from the application end between a retracted use position and extended, protective, closed position.

The test device employs a test strip selected to detect the presence or concentration of selected analytes or residues, either a single residue or classes thereof, and visually by reference of a reaction reference zone or reference line in the test strip which may be observed or measured. Usually, a control zone or line is spaced apart slightly downstream from the reference zone or lines for control purposes. The housing of the test device is applicable to a wide variety of presently employed or described test strips which are based on lateral flow or capillary flow, regardless of the nature of the particular analyte-residue test, provided only that the application or liquid contact portion of the test strip requires or uses a filtering absorbing material which moves by liquid-sample contact between a nonexpanded and an expanded state at or toward the one application end of the test device. Typically, the test strip has a support and includes, on one surfaces, a plurality of contacting, liquid-permeable, sequential zones or sections with a stationary zone, a mobile zone and, optionally, a disposal zone. The test device is particularly useful in connection with the liquid sample comprising a biological fluid; for example, urine; blood; or milk, and in the detection of antibiotics, like beta lactams or toxins, viruses and the like; however, the test device may employ one or more test strips directed to a variety of tests.

Where applicable, the test device is employed in combination with an incubator, such as a portable, electrically heated incubator with an incubation chamber which may be dimensioned to receive the test-device housing snugly therein for heating for a selected incubator time; for example, 55 to 65° C., and for a period of 1 to 10–15 minutes. The test device and incubator also include a timer, so that the incubation period may be timed by a user.

In operation, the test device with a protective covering or cap has the cover or cap removed and the application end contacted with a liquid to be tested, such as by immersion or a liquid sample pipetted into the application end for 1 to 10 seconds and then removed. The absorbing material is allowed to expand within the expansion cavity; for example, 1 to 15 seconds, then the test device placed in an incubator for a time period, then removed and the test results observed or measured.

The test device and method will be described for the purposes of illustration only in connection with certain embodiments; however, it is recognized that various changes, additions, improvements and modifications to the illustrated embodiments may be made by those persons skilled in the art, all falling within the spirit and scope of the invention.

BRIEF DESCRIPTION OF THE DRAWINGS

FIGS. 1–13 refer to FIG. 1 and FIG. 1 and FIGS. 2–13 of the drawings.

DESCRIPTION OF THE EMBODIMENTS

Figure 1:
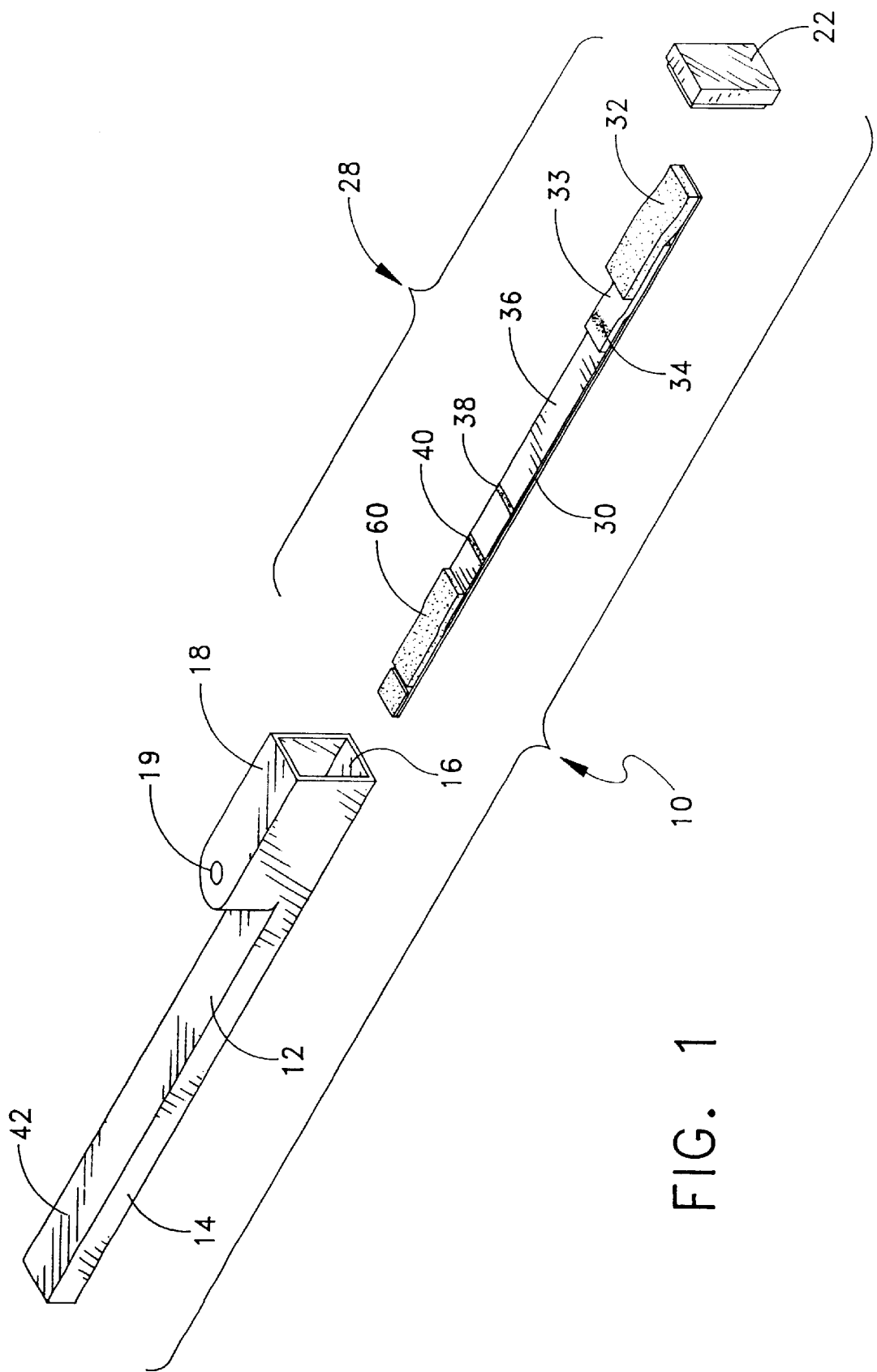
FIG. 1 is a perspective, exploded view of a molded-housing test device.
Figure 4:
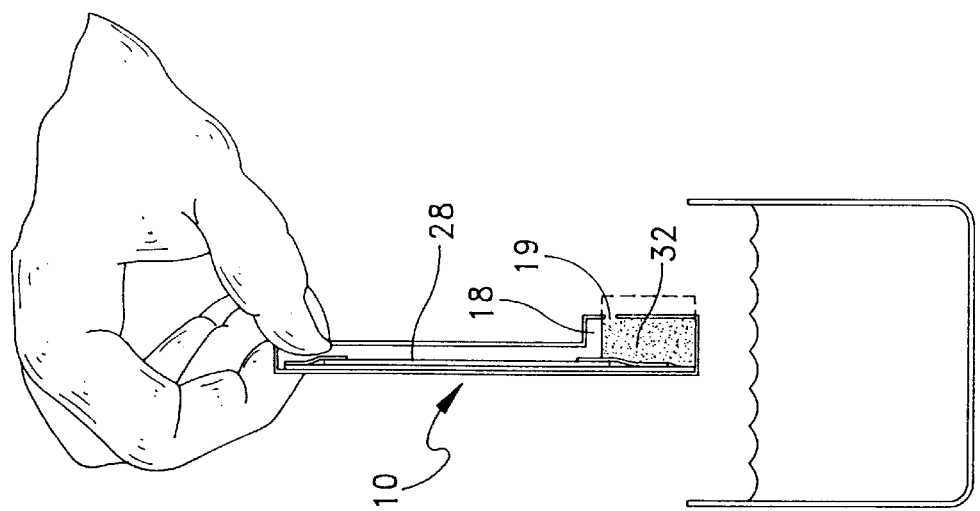
FIGS. 2, 3 and 4 are schematic, illustrative views of the use of the test device of FIG. 1.
Figure 3:
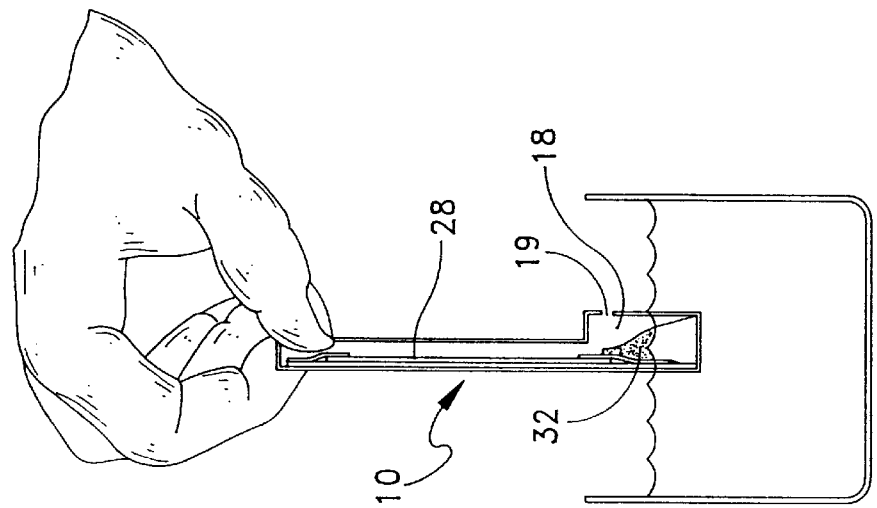

In the drawings, FIGS. 1–6 show the analyte test device 10 which includes an elongated, molded housing 12 of a one-piece, injection-molded, transparent styrene polymer to define an elongated cavity 14 with an open end 16, and having an enlarged, rectangular application cavity 18 at the one open application end of the housing 12. The housing includes an elongated bottom cavity formed during the injection-molding process. The housing includes an optional removable, friction-fitted or snap-on protective styrene cap 22 adapted to fit over the open application end 16 of the housing 12 and expansion apertures 19 in the top cover of the application housing cavity, to increase the efficiency of expansion of the material 32 within the test time.

The housing cavity 14 includes therein on the bottom surface a lateral-flow test strip 28 adapted to detect the presence of an analyte in a liquid sample, such as milk. The test strip includes an elongated, adhesive, support or backing strip 30 with a plurality of sequential layers comprising a rectangular pad of dry, compressed, cellulosic material 32 as a liquid-sample absorbent secured to the face surface of the support strip 30 at the one application end. The pad 32 is selected to expand in contact with the milk, to fill 35 the expansion cavity 18 which the pad 32 mimics in two dimensions. For example, with milk, the pad would be about 3–4 mm by 12–14 mm, while the cavity 18 would be about 5–6 mm by 15–16 mm by 4–6 mm in height. The expansion cavity may be dimensioned to be about 60% to 30% less than the full expansion of the sponge material.

The support strip 30 includes a treated, mobile-phase, support layer 33 with a visible receptor-probe area 34, a stationary-phase layer 36 which includes a reference line 38 and a control line 40 for the analyte to be detected, and a cellulosic absorbent pad 60 at the distal end of the support strip 30 to capture excess liquid sample. The housing 12 includes a transparent top cover 42 for visual observation of the reference line 38 and control line 40. The test strip 28 is placed and positioned loosely in the elongated cavity 14, with the pad 32 positioned beneath the expansion cavity 18, and the pad extending generally to about or slightly beyond the plane of the open application end, and the end covered prior to use by the protective cap 22.

Figure 2:
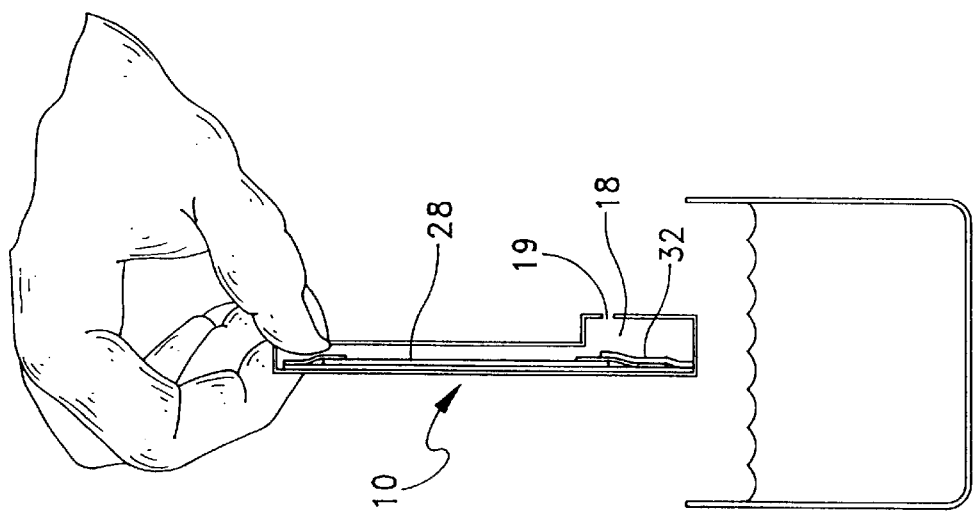
Figure 5:
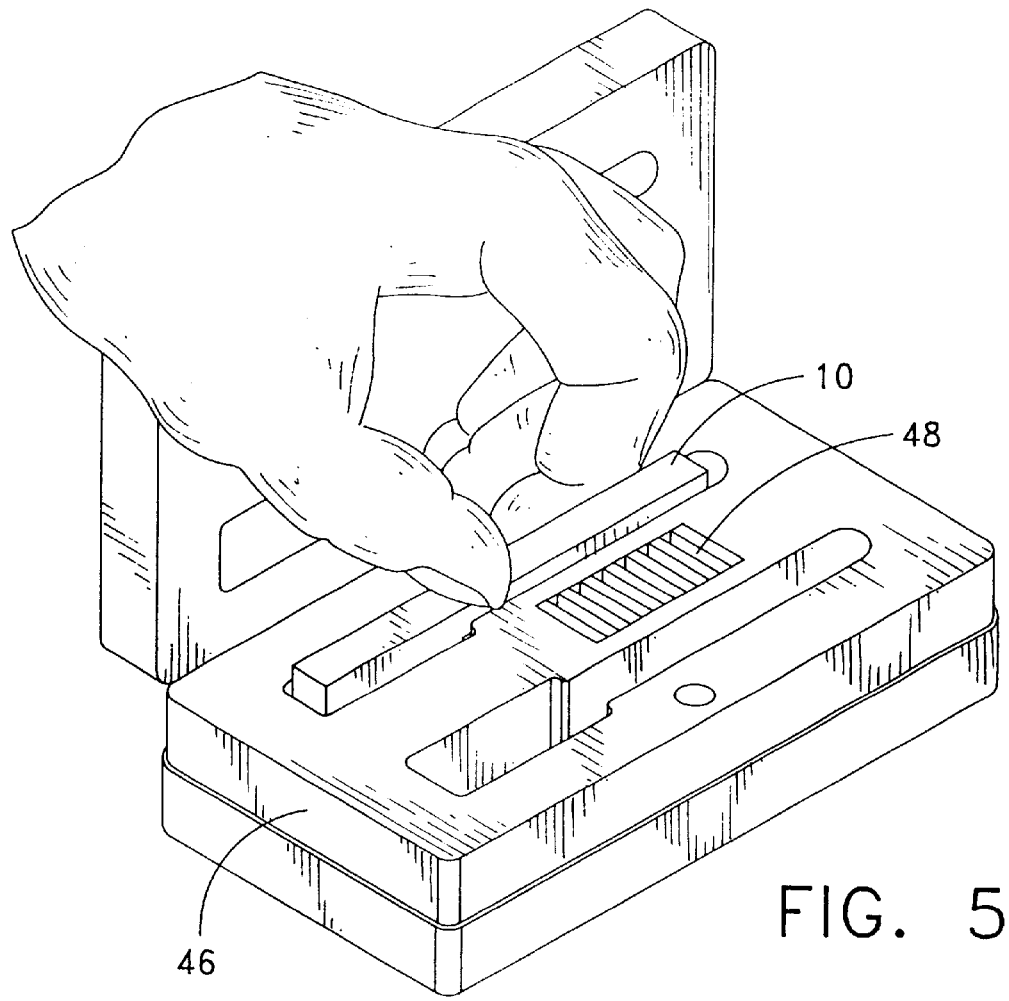
FIG. 5 is a perspective view of an incubator and the test device with a liquid sample.
Figure 6:
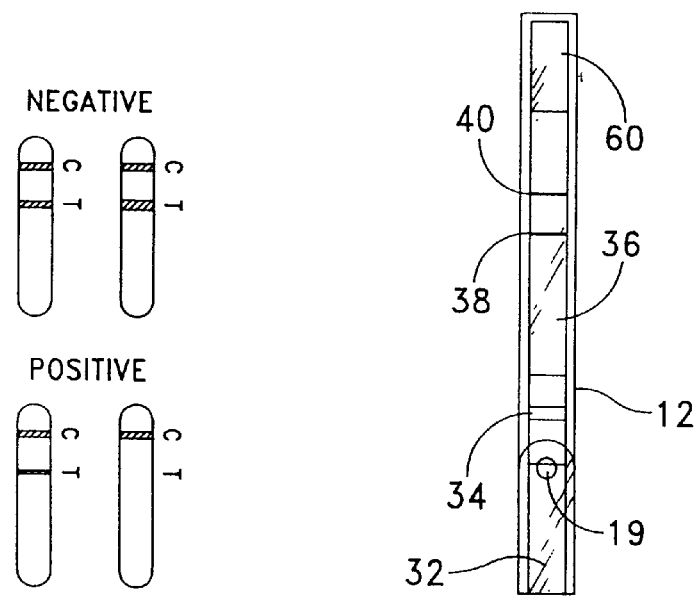
FIG. 6 is an enlarged, front-plan view of the test strip of FIGS. 1–5, with enlarged, front, sectional views of positive and negative test results.
Figure 7:
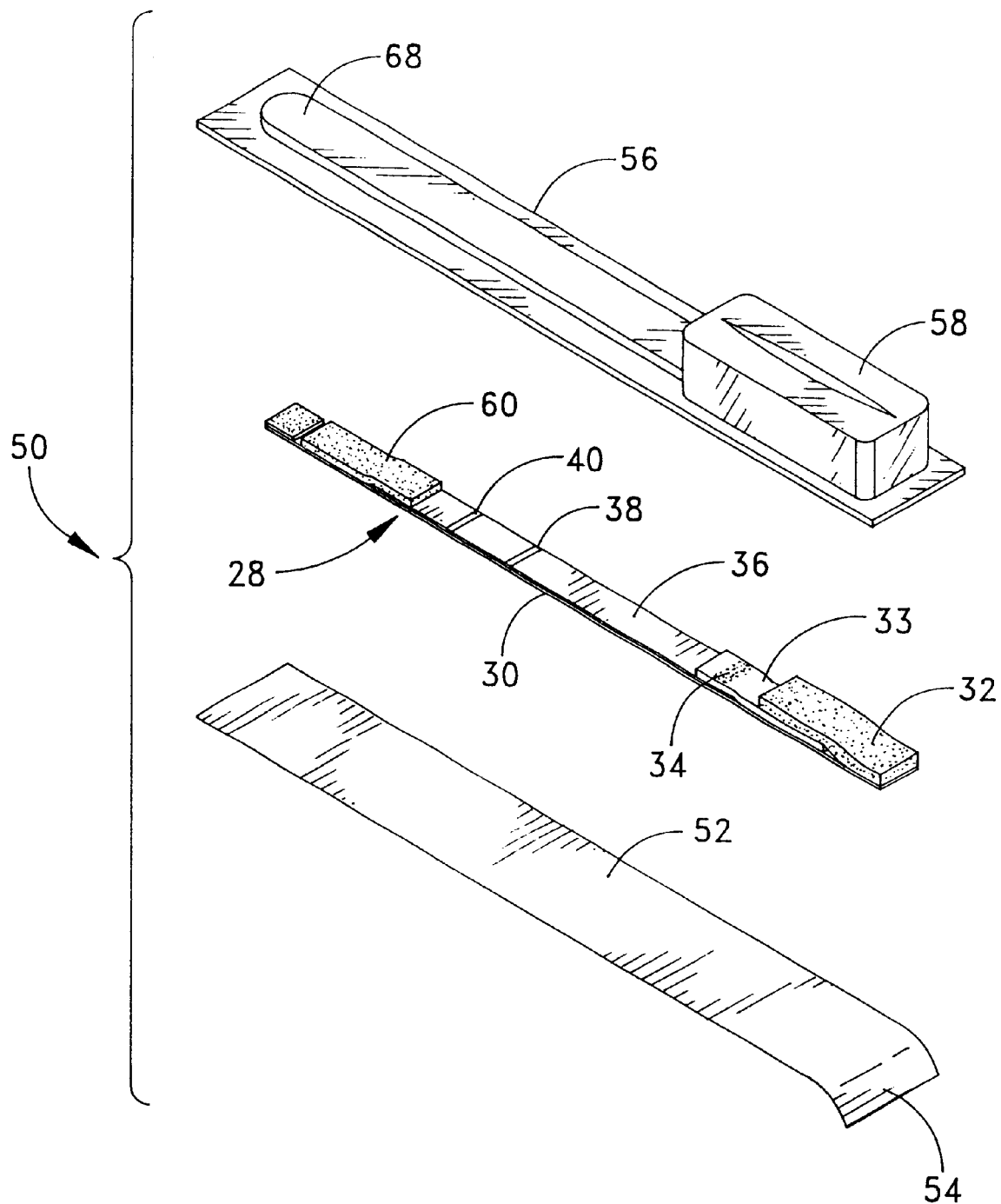
FIG. 7 is a perspective, exploded view of a blister-pack test device.

In operation, the cap 22 is removed prior to use and the open application end of the housing 12 inserted briefly (1 to 10 seconds) in the liquid; for example, milk, to be tested employing the elongated housing 12 as a handle (see FIG. 2). The test device 10 is removed and the pad 32 allowed to expand to fill the expansion cavity 18 and to start the lateral flow of the milk sample through the test strip 28 (2 to 6 minutes) (see FIGS. 3 and 4). Preferably, cap 22 is inserted to protect against cross-contamination, and the test device then placed in a horizontal position, with the application cavity 18 extending downwardly in an electric-heated incubator 46 with a cavity 47 shaped to receive the test device, and incubation carried out; for example, 1 to 8 minutes,the incubation temperature observed through the temperature-indicator scale 48 (see FIG. 5). The incubated test device 10 is then removed and reversed, and the front view of the test device with reference line 38 and control line 40 observed (see FIG. 6). The line readings for positive and negative controls are illustrated in FIG. 6 adjacent the front view of the test device 10. In the sponge material 32, expansion is controlled by the expansion cavity 18 volume and size, resulting in the sponge material 32 completely filling the cavity 18 with a preselected volume of liquid; for example, 0.1 to 1.0 ml, so the amount of liquid sample taken in for the test is controlled to the correct amount. The dimensions of the expansion cavity 18 prevent the sponge material 32 from full expansion, so that pressure is maintained in the expanded sponge (see FIG. 4) to aid in forcing capillary-lateral flow of the liquid sample through the test strip 28 in the housing 12.

The drawings in FIGS. 7–13 illustrate a further embodiment of the test device 50 in a transparent blister package which includes a transparent-tape plastic seal strip 52 with a peel tag 54 at one end, and a transparent blister package 56 adhesively secured to the strip 52, to enclose a test strip 28 therein. The blister package 56 includes an elongated cavity 68 to hold strip 28 and an expansion cavity-housing 58 at the one end to form a generally toothbrush-shaped cavity within the plastic blister package 56 and strip 52. The selected test strip 28 is sealed and enclosed within the transparent blister package.

Figure 8:
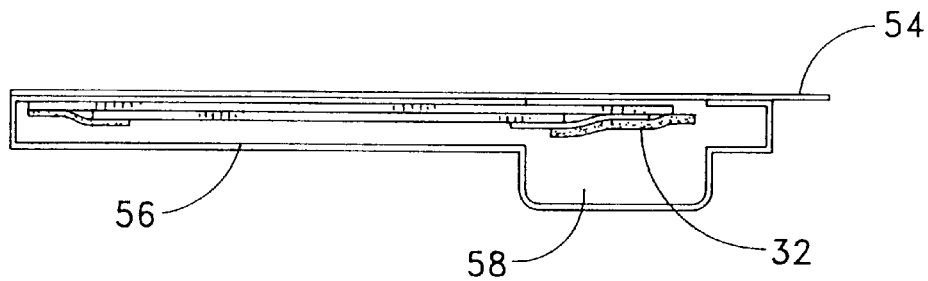
FIGS. 8, 9 and 10 are schematic, illustrative, side views of the use of the test device of FIG. 7.
Figure 9:
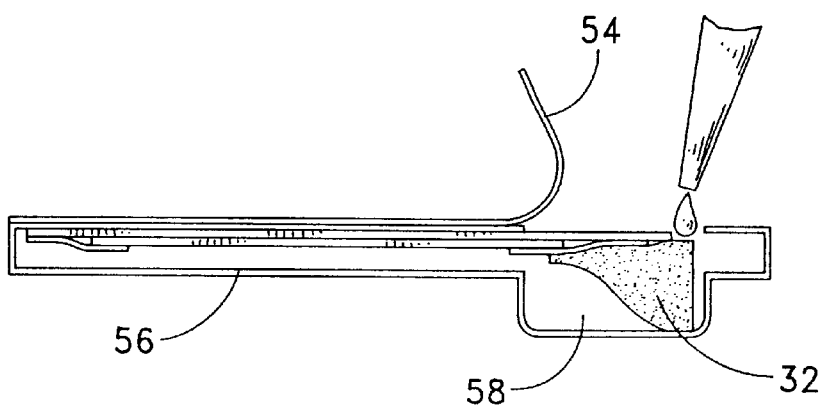
Figure 10:
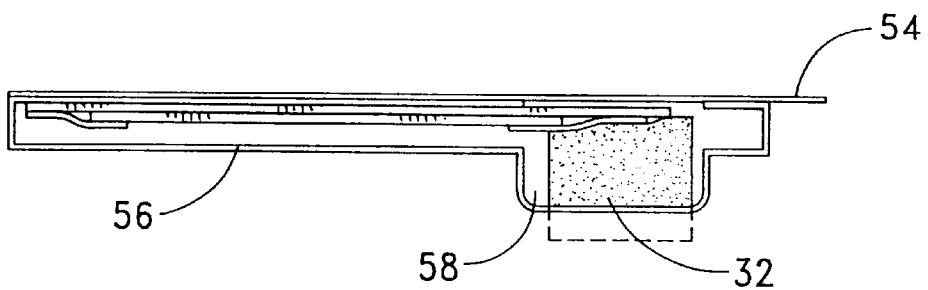

FIG. 8 shows a side sectional view of the blister-package test device 50 prior to use. FIG. 9 shows the blister-package test device 50 with one end peeled back by peel tab 54, to expose the expansion housing cavity 58 and the dry filter-absorbent sponge pad 32 of the test strip 28, so that a defined amount of a liquid sample can be added; for example, by pipet, as shown. FIG. 10 illustrates the test device 50 after addition of the liquid sample, and with the peel tab resealed and with the sponge pad 32 fully expanded by the liquid sample within housing cavity 58 and ready to incubate.

Figure 11:
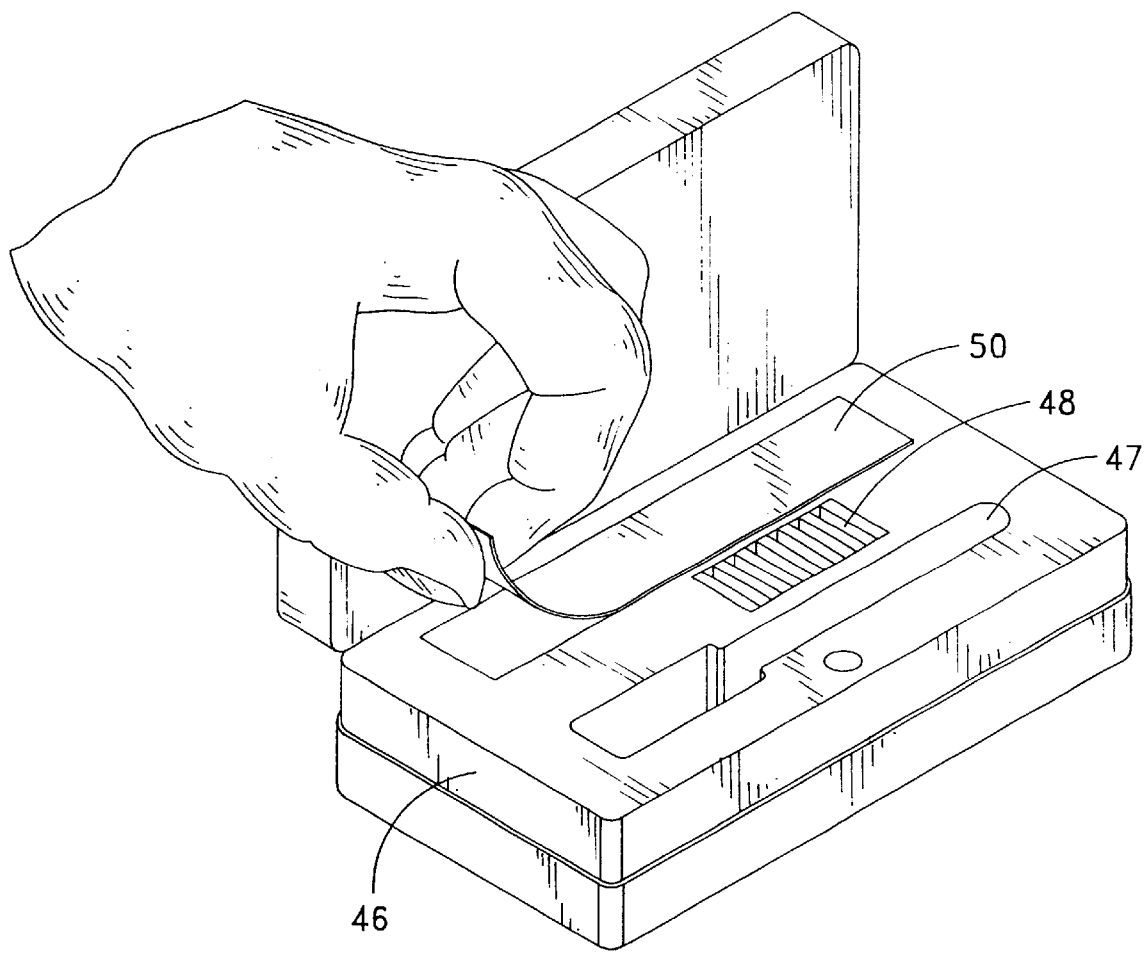
FIGS. 11 and 12 are perspective views of an incubator and the test devices of FIG. 7 with a liquid sample.
Figure 12:
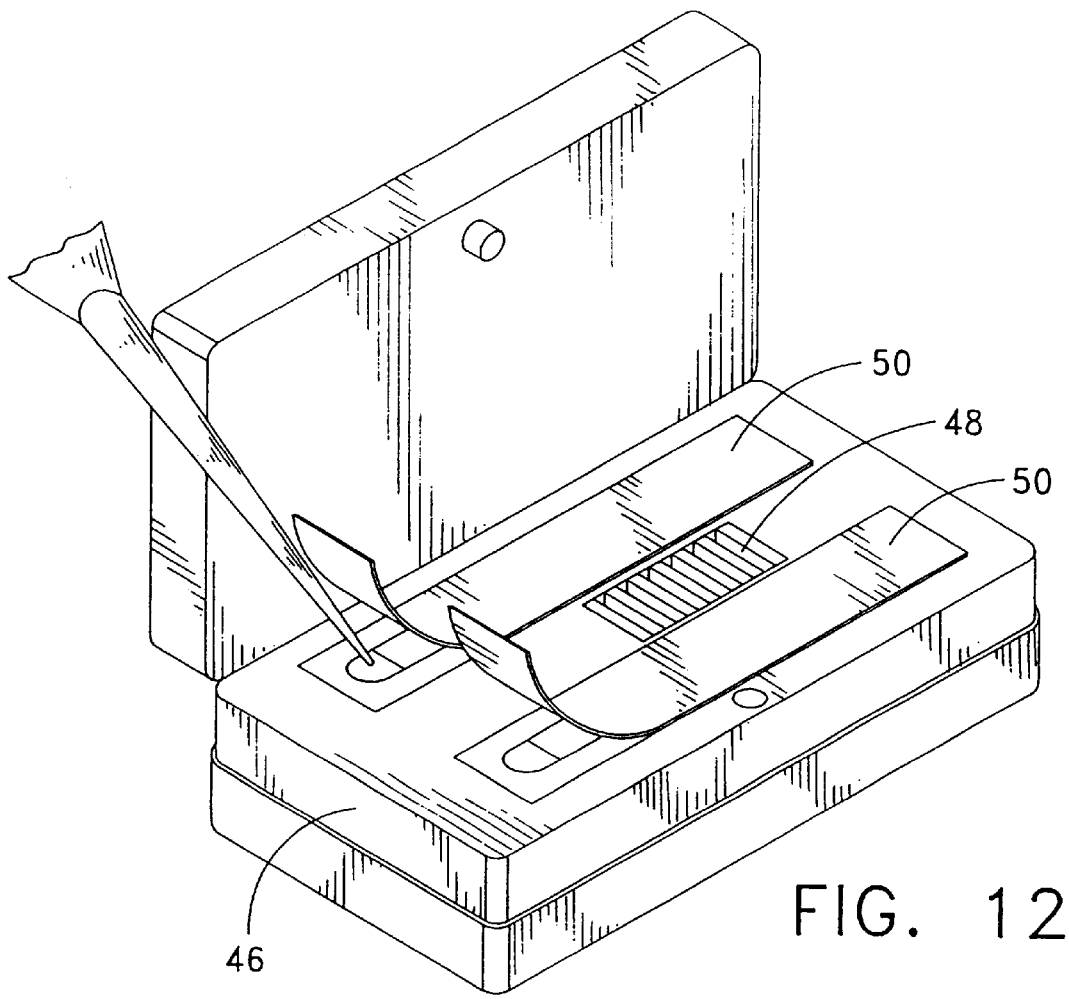
Figure 13:
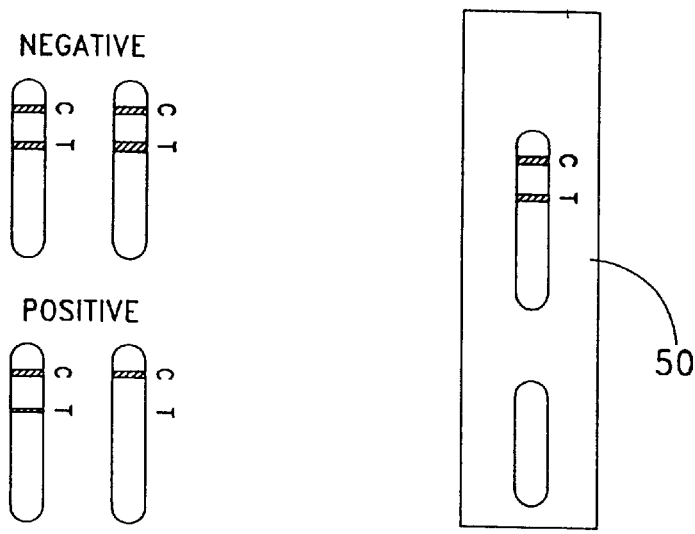
FIG. 13 is an enlarged, front-plan view of the test strip of FIGS. 7–12, with enlarged, front, sectional views of positive and negative test results.

FIG. 11 illustrates the test device 50 upside down and placed in one of two cavities 47 in an incubator 46. FIG. 12 illustrates the technique of adding the liquid sample (see FIG. 9) with pipet, while the peel tab 54 is pulled away from the end of the test device 50 in the incubator, the test device sealed (see FIG. 10) and incubated. The test results of the completed test may then be read through the transparent top cover of blister package 56, as shown in FIG. 13, to provide positive or negative test results.

The test; for example, the inhibition assay test, strip 28, selected for beta lactams in milk, is a quick test for beta lactams in comingled raw and pasteurized milk. In operation, the incubator 46 temperature gauge 48 is checked to ensure an incubator temperature of 55° C.; for example, temperature indicator 48 may be colored; for example, green, for use. The test device 50 is placed on one of the incubator 46 cavities 47, with the flat side facing up and the peel tab 54 peeled back far enough to expose the sponge pad 32; for example, ½ of an inch. The milk to be tested is mixed thoroughly before testing, and about 0.5 ml added by pipet to the exposed sponge pad 32 and the adhesive tape tab 54 resealed by hand pressure, and the incubator 46 cover closed. The test device 50 is incubated, for example, at least 6 to 8 minutes and then removed from the incubator 46 and held vertically and a comparison made within about 1 hour between the test or reference line 38 with the control line 40. If no control line 40 appears, the test is invalid. A negative test is when the reference line 38 is the same or darker than the control line 40. A positive test is indicated when the test or reference line 38 is absent or clearly lighter than the control line 40.

In more detail, the test device 10 capable of detecting analytes in biological fluids comprises the following components:

a) A compressed material, such as cellulose, that is capable of absorbing said biological fluid and acting as a prefilter to remove coarse contaminants, such as hair, dirt, etc. Said compressed material 32 is sized to absorb a fixed amount of sample required to complete the assay. This compressed material 32, when expanded and contacting the inside wall of housing 12, causes sufficient pressure to drive capillary flow along the components 32 and 36 in the time required (3 to 8 minutes) for a marketable test. Said component 32 overlaps said component 36 1 to 10 mm such that, when an aqueous sample, such as milk, is added to component 32, the sample will flow onto said component 36.

b) A housing 12 for said components 30, 32, 33, 34, 36, 38 and 40. A housing should be used to allow for addition of biological sample, either by dipping, pouring or pipetting. Said housing is constructed of either a flexible or hard material, such as polystyrene, polypropylene, or polyethylene.

c) A mobile-phase support pad 33 made of polyester, polyethylene or glass fiber that acts as a secondary filter for removal of less coarse materials (somatic cells). The support has been pretreated with a chemical solution, such as 0.01 to 0.2 M sodium citrate pH 6–8, capable of neutralizing interferences found in biological samples. The mobile-phase support pad 33 overlaps said component 36 by 1 to 4 mm.

d) A mobile phase comprising:

i) highly specific binding proteins or monoclonal antibodies capable of binding to an analyte and titrated to a known concentration to make unavailable for further reaction/detection a known amount of analyte. This unavailability for further reaction/ detection allows for the adjustment of a detection level of one or more analytes to a specified level of concern. For example, in ceftiofur, a beta-lactam with a tolerance level of 50 ppb in milk, sensitivity can be changed from 5 ppb to between 40–50 ppb by the addition of a monoclonal antibody specific for ceftiofur. The specific monoclonal antibody removes a specific analyte from binding to a receptor or antibody which is capable of binding a family of related compounds; and ii) highly purified proteins; for example, beta-lactam receptor or anti-tet lgG, prepared by affinity purification and/or a combination of hydrophobic/ion-exchange HPLC which are then attached to a colored, fluorescent, or infrared probe 34 which can be observed by optical/instrumental means or both. Attachment of proteins to a probe is called binding protein/probe complex; and iii) mobile phase is sprayed, using, a machine by Ivek, Biodot, or Camag, or absorbed onto pad 33 in a solution containing 5 to 20% sugar, such as sucrose or trehalose, 5 to 20% protein, such as BSA or Primatone, 5 to 100 mm of a buffer solution (phosphate or Trizma base) with a final pH of between 6–8. The mobile phase is sprayed on the upper portion of the mobile-phase support pad 33, such that component 34 does not overlap said component 32, but rather said component 33 overlaps said component 33 by placing the topmost portion of said component 32 1 to 7 mm before the sprayed portion of said component (32). A stationary phase membrane 36 consisting of nitrocellulose or nylon which has multiple reaction zones present and comprising:

capture zone(s) is/are formed by spraying in a test line 38 using a spraying instrument, such as Ivek, Biodot or Camag. The purpose of said capture zone is to capture unreacted binding protein/probe complex for viewing or measurement. Capture zone(s) consist of an analyte of detection; that is, penicillin G or a member of said analyte family; that is, beta-lactams, coupled to a carrier protein; that is, BSA, IgG, KLH, suspended in a 5 to 100 mm buffer solution (phosphate or Trizma base) at a pH range of 6–8. Total protein concentration of the antibody solution ranges from 0.2 to 100 mg/ml and;

a control zone is formed by spraying in a line 40 using a spraying instrument, such as Ivek, Biodot or Camag. The purpose of said control zone is to capture binding protein/probe complex that has not bound to said capture zone(s). The control zone consists of an antibody specific to the binding protein/probe suspended in 5 to 100 mm of a buffer solution (phosphate or Trizma) at a pH range of 6 to 8. Total protein concentration of antibody solution ranges from 0.2 to 100 mg/ml;

A comparison of the control zone 40 to the capture zone(s) 38 yields test result. Typically, if the control zone is darker than the capture zone(s), analyte is, present at detection level or greater (see FIG. 6 and FIG. 13)

A plastic backing 30 with adhesive is employed for the mounting of zones 32, 33, 36, and 40.

A disposal pad made of pressed cellulose or other absorbent material is employed to keep the sample flow consistent and to retain the reacted sample. The disposal pad overlaps the stationary-phase membrane 36 by 1 to 5 mm.

An aqueous biological sample is added to component 32 of a test device 10. Component 32 serves as a sample pad which expands as it absorbs the sample. Component 32 overlaps component 33, and the fluid flows onto the mobile-phase support where the mobile-phase materials dissolve into the biological fluid. Analytes present in the sample begin binding with the specific binding protein(s) 34 attached to the probe. At the same time, specific unbound antibodies or binding proteins will bind with specific analytes to adjust their sensitivity to the test. The mobile-phase supports pad 33 overlaps the stationary-phase membrane E(36), and the biological fluid, along with the mobile-phase materials 34, continue to react as all flow up the stationary phase. When the binding protein/probe complex reaches the capture zone, a portion of the binding protein/probe complex will bind to the capture zone. In a positive sample, analyte in the sample will have bound to the binding protein/probe complex, reducing the amount of binding protein/probe complex capable of binding to the capture zone. When the material reaches the control zone, a portion of binding protein/probe complex will bind the control zone. Excess reagent is then absorbed into the disposal pad.

In a negative sample, reagents are titrated, so that the capture zone will have the same or preferably a greater amount of the probe binding to it than in the control zone. Conversely, in a positive sample, the control zone will have a greater amount of the probe binding to it than the capture zone.

In one manifestation of this test device 10, a beta-lactam test is made to assay for beta-lactams in milk at a safe level. A partially purified beta-lactam receptor from BST (*acillus stearothermophilus*) is bound to a colloidal gold sol to make a beta-lactam binding protein/gold bead probe 34. This is sprayed onto the mobile-phase support along with monoclonal antibodies to ceftiofur and cephapirin, to reduce the sensitivity of these two antibiotics to a safe level. To the capture line 38 is sprayed a ceforanide-BSA conjugate, and to the control lines 40 is sprayed an antibody to the BST beta-lactam receptor. A raw-milk sample (0.5 ml) is applied to the sample pad 32 by pipette in test device 50 or dipping the open end 16 of housing 12 in test device 10, and the test strip 28 is incubated at 55° C. After 8 minutes, the test strip is removed from the incubator 46 and analyzed. If the capture (test) lined 38 is darker or the same color as the control line, the 40 sample is negative, and, if the capture line is lighter than the control line, the sample is positive.

Test results are as follows:

TABLE 1

Beta-lacterix assay in milk using lateral flow test device.

| Number of assays | sample | result |
|---|---|---|
| 30 | zero control | all negative |
| 10 | penicillin G at 5 ppb | all positive |
| 10 | penicillin G at 4 ppb | 5 positive, 5 negative |
| 10 | penicillin G at 3 ppb | 3 positive, 7 negative |
| 10 | ampicillin at 6 ppb | all positive |
| 10 | ampicillin at 4 ppb | all positive |
| 10 | ampicillin at 3 ppb | 5 positive, 5 negative |
| 10 | amoxicillin at 6 ppb | all positive |
| 10 | amoxicillin at 4 ppb | 8 positive, 2 negative |
| 10 | amoxicillin at 3 ppb | 4 positive, 6 negative |
| 10 | ocftiofur at 30 ppb | 3 positive, 7 negative |
| 10 | ocftiofur at 40 ppb | 8 positive, 2 negative |
| 10 | ocftiofur at 50 ppb | 10 positive |
| 10 | cephapirin at 12 ppb | 2 positive, 8 negative |
| 10 | cephapirin at 15 ppb | 5 positive, 5 negative |
| 10 | cephapirin at 20 ppb | 9 positive, 1 negative |

The described test is an inhibition-type assay. Analyte in the sample binds with a beta-lactam binding protein/gold bead probe and inhibits binding to a stationary beta-lactam bound to the surface of the membrane. Addition of a specific monoclonal antibody to ceftiofur has altered its inhibition level from approximately 5 ppb to between 40 and 50 ppb. Addition of a specific monoclonal antibody to cephapirin has reduced its sensitivity from approximately 3 ppb to between 15 to 10 ppb.

The test device of the invention may be used with test strips for detecting a variety of analytes, such as toxins like alfatoxins; as well as beta-lactams like penicillin, ampicillin, amoxicillin, cloxacillin, dicloxacillin, oxacillin, ceftiofur, and cephapirin; tetracyclines like chlortetracycline, oxytetracycline and tetracycline; sulfoanamides like sulfadimidine, sulfadimethoxine, sulfamerazine, sulfathiazole and sulfadiazine; macrolides like erythromycin, spiramycin and tylosin; aminoglycocides like gentamicin, neomycin and DH/streptomycin; and others like dipsone, chloramphenicol, novobiocin, spectinomhcin and trimethoprim, to detect the maximum residue-analyte limits in the sample.

What is claimed is:

1. A method for the detection of an analyte or analyte class in a liquid sample, comprising the steps of:
    a) providing a lateral flow test strip within a housing, wherein a portion of the housing defines an expansion housing cavity, and wherein the test strip comprises (i) a first end, a second end, a top surface, and a bottom surface, (ii) an absorption zone proximal to the first end, the absorption zone comprising an expandable absorption material within the expansion housing cavity defined by said housing, the expansion housing cavity dimensioned to prevent full expansion of the absorption material, and (iii) a reference zone comprising one or more component(s) for detection of said analyte or analyte class;
    b) allowing a contact to form between the test strip and the liquid sample so as to allow absorption of the liquid sample into the absorption material, thereby causing the absorption material to expand within the expansion housing cavity so as to aid in forcing the liquid-sample to flow toward the reference zone; and
    c) observing changes in the reference zone as an indication of the presence or absence of the analyte or analyte class in the liquid sample.

2. The method of claim 1, wherein said test strip further comprises a disposal zone between the reference zone and the second end.

3. The method of claim 1, wherein the shape of said absorption material generally mimics two dimensions of the expansion cavity.

4. The method of claim 1, wherein the absorption material is positioned on the top surface of the test strip.

5. The method of claim 4, wherein one side of the expansion housing cavity can be opened to expose the bottom surface of the test strip.

6. The method of claim 1, wherein said contacting comprises dipping the absorption material into a source of the liquid sample.

7. The method of claim 1, further comprising the step of incubating the test strip with the liquid sample thereon.

8. The method of claim 1, wherein the housing comprises an aperture, and said method further comprises allowing air to exit the housing through the aperture.

9. The method of claim 1, wherein at least a portion of said housing is substantially transparent.

10. The method of claim 1, wherein the housing comprises a peelable seal, and said contacting comprises peeling said seal from said housing.

11. The method of claim 1, wherein said expansion housing cavity has a volume, the volume of said expansion housing cavity preventing said absorption material from expanding to more than eighty percent (80%) of its full expansion volume.

12. The method of claim 11, wherein the volume of the expansion housing cavity prevents said absorption material from expanding to more than fifty percent (50%) of its full expansion volume.

13. The method of claim 1, wherein said analyte class is a class of antibiotics.

14. The method of claim 1, wherein said liquid sample is a biological fluid.

15. The method of claim 1, wherein said observing comprises determining whether said analyte or analyte class is present in said liquid sample at or above a threshold concentration.

16. The method of claim 1, wherein said contacting comprises allowing absorption of the liquid sample in a preselected amount.

17. The method of claim 1, wherein the absorption material is a filter.

18. The method of claim 1, wherein the liquid sample comprises milk.

19. The method of claim 1, wherein the analyte comprises beta lactams.

20. The method of claim 1, wherein expansion of the absorption material is restricted by contact with a wall of the expansion housing cavity so as to control the volume of the liquid sample flowing to the reference zone.

21. The method of claim 1, wherein full expansion of the absorption material is restricted by a top internal wall of the expansion housing cavity.

22. The method of claim 1, wherein said housing comprises a blister package.

23. A method for the detection of an analyte or analyte class in a liquid sample, comprising the steps of:
  a) providing a lateral-flow test strip within a housing, the test strip comprising (i) a first end, a second end, a top surface, and a bottom surface, (ii) an absorption zone proximal to the first end, the absorption zone comprising an expandable absorption material positioned on the top surface of the test strip within an expansion cavity, the expansion cavity dimensioned to prevent full expansion of the absorption material and having one side that can be opened to expose the bottom surface of the test strip, and (iii) a reference zone comprising one or more component(s) for detection of said analyte or analyte class;
  b) allowing a contact to form between the test strip and the liquid sample so as to allow absorption of the liquid sample into the absorption material, thereby causing the absorption material to expand within the expansion cavity so as to force the liquid-sample to flow toward the reference zone; and
  c) observing changes in the reference zone as an indication of the presence or absence of the analyte or analyte class in the liquid sample.

24. A method for the detection of an analyte or analyte class in a liquid sample, comprising the steps of:
  a) providing a lateral-flow test strip within a housing, the test strip comprising (i) a first end, a second end, a top surface, and a bottom surface, (ii) an absorption zone proximal to the first end, the absorption zone comprising an expandable absorption material within an expansion cavity portion of said housing, the expansion cavity dimensioned to prevent full expansion of the absorption material, and (iii) a reference zone comprising one or more component(s) for detection of said analyte or analyte class;
  b) allowing a contact to form between the test strip and the liquid sample so as to allow absorption of the liquid sample into the absorption material, thereby causing the absorption material to expand within the expansion cavity so as to force the liquid-sample to flow toward the reference zone, wherein the housing comprises a peelable seal and said contacting comprises peeling said seal from said housing; and
  c) observing changes in the reference zone as an indication of the presence or absence of the analyte or analyte class in the liquid sample.

25. A sethod for the detection of an analyte or analyte class in a liquid sample, comprising the steps of:
  a) providing a lateral-flow test strip within a housing, the test strip comprising (i) a first end, a second end, a top surface, and a bottom surface, (ii) an absorption zone proximal to the first end, the absorption zone comprising an expandable absorption material within an expansion cavity portion of said housing, the expansion cavity having a volume and dimensioned to prevent full expansion of the absorption material, and (iii) a reference zone comprising one or more component(s) for detection of said analyte or analyte class;
  b) allowing a contact to form between the test strip and the liquid-sample so as to allow absorption of the liquid sample into the absorption material, the volume of the expansion cavity preventing said absorption material from expanding to more than eighty percent (80%) of its full volume thereby causing the absorption material to expand within the expansion cavity so as to force the liquid-sample to flow toward the reference zone; and
  c) observing changes in the reference zone as an indication of the presence or absence of the analyte or analyte class in the liquid sample.

26. The method of claim 25, wherein the volume of the expansion cavity prevents said absorption material from expanding to more than fifty percent (50%) of its full expansion volume.

27. The method of claim 25, wherein the volume of the expansion cavity prevents said absorption material from expanding to more than sixty percent (60%) of its full expansion volume.

28. The method of claim 25, wherein the volume of the expansion cavity prevents said absorption material from expanding to more than thirty percent (30%) of its full expansion volume.

* * * * *

UNITED STATES PATENT AND TRADEMARK OFFICE
CERTIFICATE OF CORRECTION

PATENT NO. : 6,475,805 B1
DATED : November 5, 2002
INVENTOR(S) : Stanley E. Charm et al.

It is certified that error appears in the above-identified patent and that said Letters Patent is hereby corrected as shown below:

<u>Column 12,</u>
Line 6, after "A", please delete "sethod" and insert -- method --.

Signed and Sealed this

Fourth Day of March, 2003

JAMES E. ROGAN
*Director of the United States Patent and Trademark Office*